(12) United States Patent
Deng et al.

(10) Patent No.: US 7,972,861 B2
(45) Date of Patent: Jul. 5, 2011

(54) METHODS FOR PERFORMING HEMATOCRIT ADJUSTMENT IN GLUCOSE ASSAYS AND DEVICES FOR SAME

(75) Inventors: Yingping Deng, Fishers, IN (US); Sherry J. Jamison, Goshen, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 1024 days.

(21) Appl. No.: 11/596,401

(22) PCT Filed: May 13, 2005

(86) PCT No.: PCT/US2005/017014
§ 371 (c)(1),
(2), (4) Date: Nov. 14, 2006

(87) PCT Pub. No.: WO2005/114163
PCT Pub. Date: Dec. 1, 2005

(65) Prior Publication Data
US 2007/0231914 A1   Oct. 4, 2007

Related U.S. Application Data

(60) Provisional application No. 60/571,389, filed on May 14, 2004.

(51) Int. Cl.
G01N 33/66 (2006.01)
G01N 33/50 (2006.01)
G01N 27/06 (2006.01)

(52) U.S. Cl. ............... 436/95; 436/63; 436/70; 436/149; 436/150; 435/14; 702/19

(58) Field of Classification Search .................. 436/63, 436/69, 70, 95, 149, 150; 422/68.1, 73, 82.01, 422/82.02; 435/14, 287.1; 600/347, 365; 702/19
See application file for complete search history.

(56) References Cited

U.S. PATENT DOCUMENTS

| | | | |
|---|---|---|---|
| 4,935,346 A | 6/1990 | Phillips et al. | |
| 5,049,394 A | 9/1991 | Howard et al. | |
| 5,049,487 A | 9/1991 | Phillips et al. | |
| 5,179,005 A | 1/1993 | Phillips et al. | |
| 5,304,468 A | 4/1994 | Phillips et al. | |
| 5,558,834 A | 9/1996 | Chu et al. | |
| 5,789,255 A | 8/1998 | Yu | |
| 5,948,695 A | 9/1999 | Douglas et al. | |
| 6,190,918 B1 | 2/2001 | Chu et al. | |
| 6,210,591 B1 | 4/2001 | Krivitski | 210/739 |
| 6,475,372 B1 * | 11/2002 | Ohara et al. | 205/777.5 |
| 6,890,421 B2 * | 5/2005 | Ohara et al. | 205/777.5 |
| 7,018,843 B2 | 3/2006 | Heller | |
| 7,049,354 B2 | 5/2006 | Yamoto et al. | |
| 7,323,315 B2 | 1/2008 | Marfurt | |
| 2003/0064525 A1 | 4/2003 | Liess | 436/149 |
| 2003/0096420 A1 | 5/2003 | Heller | 436/63 |
| 2004/0021469 A1 | 2/2004 | Blomberg et al. | 27/416 |
| 2004/0079652 A1 * | 4/2004 | Vreeke et al. | 205/777.5 |
| 2005/0176153 A1 * | 8/2005 | O'hara et al. | 436/70 |
| 2007/0062822 A1 | 3/2007 | Fujiwara et al. | |
| 2007/0131565 A1 | 6/2007 | Fujiwara et al. | |
| 2007/0138026 A1 | 6/2007 | Fujiwara et al. | |
| 2008/0248581 A1 * | 10/2008 | Chu et al. | 436/66 |

FOREIGN PATENT DOCUMENTS

| | | |
|---|---|---|
| EP | 0 928 967 A2 | 7/1999 |
| EP | 0 928 967 A3 | 5/2000 |
| EP | 1 111 378 A2 | 6/2001 |
| EP | 1 202 059 | 5/2002 |
| EP | 1 202 061 | 5/2002 |
| EP | 1 394 545 A1 | 3/2004 |
| EP | 1 411 348 A1 | 4/2004 |
| WO | WO 00/73785 A2 | 12/2000 |
| WO | WO 01/57239 A2 | 8/2001 |
| WO | WO 01/57510 A2 | 8/2001 |
| WO | WO 02/14535 | 2/2002 |

OTHER PUBLICATIONS

Written Opinion corresponding to International Patent Application Serial No. PCT/US2005/017014, European Patent Office, dated May 13, 2005, 5 pages.
International Search Report corresponding to International Patent Application Serial No. PCT/US2005/017014, European Patent Office, dated May 13, 2005, 4 pages.

* cited by examiner

Primary Examiner — Maureen M Wallenhorst
(74) Attorney, Agent, or Firm — Nixon Peabody LLP

(57) ABSTRACT

Methods and devices for performing in situ hematocrit adjustments during glucose testing using glucose-monitoring products and using those adjusted values to estimate the hematocrit value of blood samples to reduce or eliminate the assay bias caused by the different hematocrit levels of blood samples. One method involves measuring the glucose value, $Glu_m$, of the blood sample; measuring the resistance of the blood sample ($R_{cell}$) using a biosensor reagent; measuring the resistance of plasma ($R_{plasma}$) using the biosensor reagent; determining the calculated resistance of red blood cells, $R_{RBC}$, of the blood sample according to the relationship $$R_{RBC} = R_{cell} - R_{plasma};$$

calculating the percent hematocrit, $\% Hct_c$, of the blood sample; determining whether to adjust the glucose value, $Glu_m$, to an adjusted glucose value, $Glu_{adj}$; and using the percent hematocrit, $\% Hct_c$, and either the glucose value, $Glu_m$, or the adjusted glucose value, $Glu_{adj}$, to adjust for any bias of the biosensor reagent.

28 Claims, 2 Drawing Sheets

METHODS FOR PERFORMING HEMATOCRIT ADJUSTMENT IN GLUCOSE ASSAYS AND DEVICES FOR SAME

CROSS REFERENCE TO RELATED APPLICATION

This application claims priority to Application No. 60/571,389 filed on May 14, 2004, which is incorporated by reference in its entirety.

FIELD OF THE INVENTION

The invention relates to methods and devices for correcting the glucose bias in glucose-monitoring products to provide more accurate glucose readings of blood samples. In particular, the invention relates to methods and devices for performing in situ hematocrit adjustments during glucose testing using glucose-monitoring products and using those adjusted values to estimate the hematocrit value of blood samples to reduce or eliminate the assay bias caused by the different hematocrit levels of blood samples.

BACKGROUND OF THE INVENTION

Hematocrit is the volume of red blood cells (RBC) expressed as a percentage of the volume of RBC in a whole blood sample. The normal hematocrit range for a typical human being is about 40 Vol. % to about 45 Vol. %. In extreme cases, the hematocrit range for a human beings can range from about 20 Vol. % to about 60 Vol. %.

Prior methods for estimating the hematocrit value of a blood sample have been based upon physical and/or chemical properties of the whole blood sample based upon the amount of red blood cells in the whole blood sample. For example, the hematocrit value of a whole blood sample has been estimated by measuring the RBC volume after centrifugation by conductivity, resistivity, impedance, and/or concentration of markers such as $Na^+$ cations in red blood cells or heme concentration in hemoglobin and other properties which may be distinguished based on the amount of RBC in whole blood samples. Although hematocrit values of whole blood samples have been measured routinely in the clinical or laboratory setting, hematocrit values are not commonly measured with glucose-monitoring products such as home meters.

One device that may be used to determine the hematocrit value of a whole blood sample in glucose-monitoring products or systems is a biosensor or biosensor reagent. The dependence or sensitivity of a biosensor reagent to hematocrit is one factor used to determine the accuracy and quality of a glucose-monitoring product as the hematocrit level of a blood sample can impact the glucose level of the blood sample being tested.

One problem with using current biosensor reagents to determine the hematocrit value and, consequently, the glucose value of a whole blood sample involves RBC interference. Red blood cells are small particles in blood samples that block a biosensor reagent's ability to measure the glucose level of the blood sample. RBC interference contributes to a bias reading or a glucose bias in the biosensor reagents of glucose-monitoring products.

For a given sample of whole blood, the measurement of the percent glucose in a blood sample should not vary whether the sample is tested at a level of 20 Vol. % hematocrit or a level of 60 Vol. % hematocrit. However, due to RBC interference, there is a percentage bias in the glucose reading that is detected by the biosensor reagent that varies based upon the level of hematocrit in the sample. The bias reading caused by the hematocrit content of a blood sample is commonly referred to as "hematocrit effect."

It is common for glucose biosensor reagents in glucose-monitoring products to exhibit hematocrit effect. For example, in some current glucose-monitoring products, the glucose assay bias for approximately 20 Vol. % RBC in whole blood to approximately 60 Vol. % RBC in whole blood generally ranges from about 15 Vol. % to about 20 Vol. %. In general, the higher the glucose bias, the less accurate the glucose reading and the worse the performance of the glucose-monitoring product. In contrast, the lower the glucose bias, the more accurate the glucose reading and the better the performance of the glucose-monitoring product.

The bias reading caused by the hematocrit content of a blood sample can have an adverse effect on patients. Patients who have low hematocrit levels may misinterpret their glucose value as being too high because of the glucose bias and think they need insulin to bring their high glucose level down. Because the actual glucose level is not as high as the perceived glucose level, patients may drop their glucose level too low by unnecessarily taking too much insulin. Conversely, patients who have high hematocrit levels may misinterpret their glucose value as being normal when it is actually high because of the glucose bias. Because the actual glucose level is not as low as the perceived glucose level, patients may consistently forego or miss needed treatment, leading to long term medical complications.

One method for determining the glucose bias of a glucose biosensor reagent in a glucose-monitoring product is to measure the glucose value of the blood sample ($Glu_m$) using a glucometer and determine the reference value of the glucose content ($Glu_{ref}$). The value for $Glu_m$ may be measured on a glucose-monitoring product such as a home meter. The value for $Glu_{ref}$ is determined independently of the glucose-monitoring product using a reference method and a reference instrument. $Glu_{ref}$ is typically determined in a clinical or laboratory setting. The percentage of glucose bias can be determined according to the relationship set forth in Equation 1:

$$(Glu_m - Glu_{ref}) * 100 / Glu_{ref} \qquad (Eq. 1)$$

Determining the percentage of glucose bias using this method is only practical if the value for $Glu_{ref}$ can be measured for every blood sample, but this is typically not feasible for users of glucose-monitoring products. In addition, this method of determining the percentage of glucose bias is inconvenient as the value for $Glu_{ref}$ is measured in a clinical or laboratory setting.

There is, therefore, a need for methods for correcting and minimizing the glucose bias in glucose-monitoring products which is caused by the hematocrit effect. There is also a need for methods for correcting the glucose bias, if any, in glucose monitoring products such as home meters without the need for patient samples to be brought to a clinical or laboratory setting. There is also a need for devices which can perform such adjustments without the need for patients to bring blood samples to a clinician or laboratory for determining the glucose bias of the biosensor reagent.

SUMMARY OF THE INVENTION

In general, the invention relates to methods for adjusting glucose bias, if any, of a blood sample in a glucose-monitoring product. One method involves measuring the glucose value, $Glu_m$, of the blood sample; measuring the resistance of the blood sample ($R_{cell}$) using a biosensor reagent; measuring the resistance of plasma ($R_{plasma}$) using the biosensor reagent; determining the calculated resistance of red blood cells, $R_{RBC}$, of the blood sample according to the relationship $$R_{RBC}=R_{cell}-R_{plasma};$$

calculating the percent hematocrit, % $Hct_c$, of the blood sample; determining whether to adjust the glucose value, $Glu_m$, to an adjusted glucose value, $Glu_{adj}$; and using the percent hematocrit, % $Hct_c$, and either the glucose value, $Glu_m$, or the adjusted glucose value, $Glu_{adj}$, to adjust for the bias of the biosensor reagent, if any.

The invention further relates to meters that correct the glucose bias of a blood sample in a glucose-monitoring product. One meter includes means for measuring the glucose value, $Glu_m$, of the blood sample; means for measuring the resistance of the blood sample ($R_{cell}$) using a biosensor reagent; means for measuring the resistance of plasma ($R_{plasma}$) using the biosensor reagent; means for determining the calculated resistance of red blood cells, $R_{RBC}$, of the blood sample according to the relationship $$R_{RBC}=R_{cell}-R_{plasma};$$

means for calculating the percent hematocrit, % $Hct_c$, of the blood sample; means for determining whether to adjust the glucose value, $Glu_m$, to an adjusted glucose value, $Glu_{adj}$; and means for using the percent hematocrit, % $Hct_c$, and either the glucose value, $Glu_m$, or the adjusted glucose value, $Glu_{adj}$, to adjust for the bias of the biosensor reagent, if any.

BRIEF DESCRIPTION OF THE DRAWINGS

The foregoing and other advantages of the invention will become apparent upon reading the following detailed description and upon reference to the drawings.

DESCRIPTION OF EMBODIMENTS OF THE INVENTION

Figure 1:
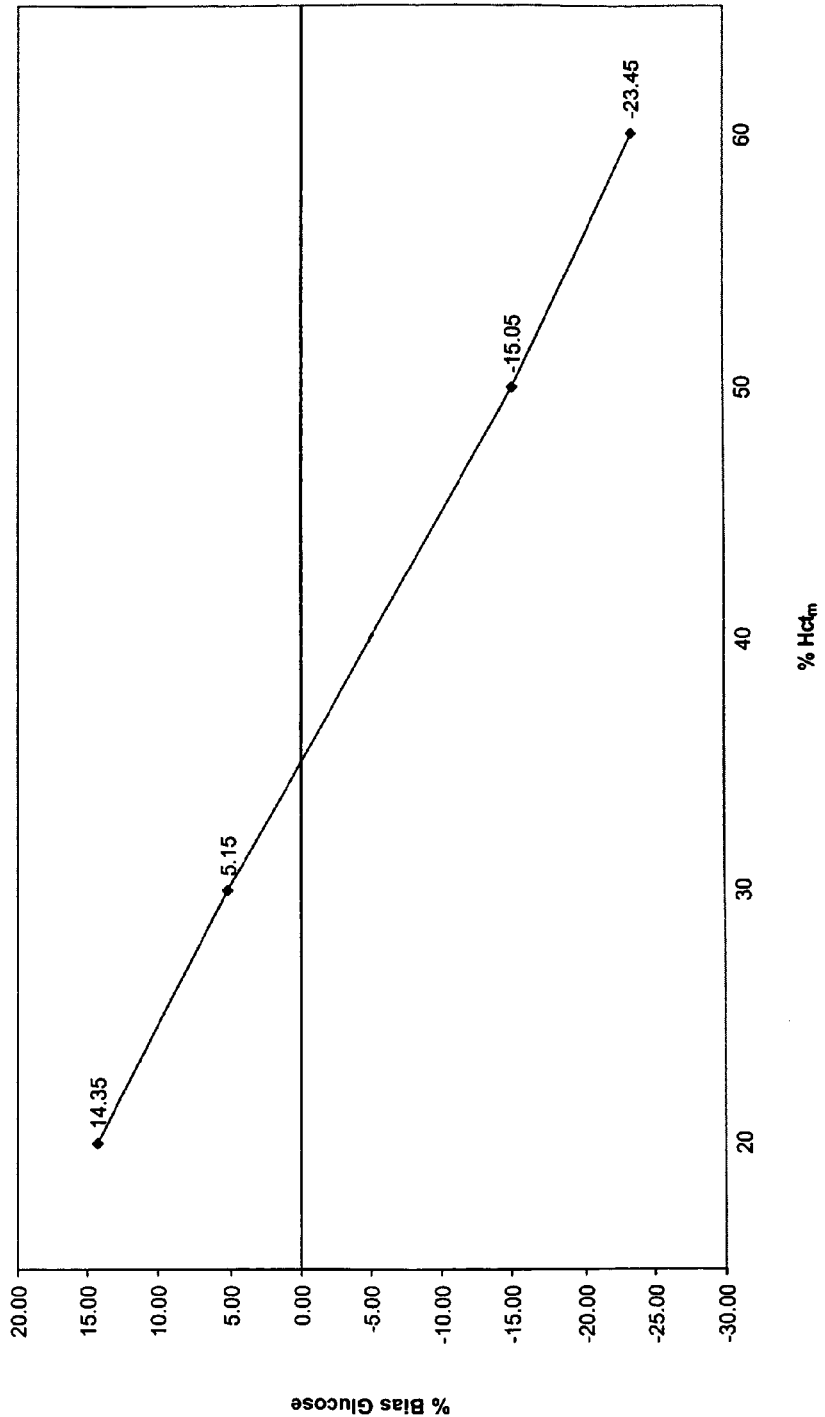
FIG. 1 is a plot showing the percent glucose bias versus the percent hematocrit calculated for a blood sample.

Embodiments of the invention are, in part, based on the discovery that the performance of glucose-monitoring products may be improved by lowering the glucose bias, if any, of the biosensor reagent measurement in glucose-monitoring products. It has been discovered that by using the methods and devices described herein, a more accurate glucose reading can be obtained from the biosensor reagent measurement in glucose-monitoring products. By obtaining a more accurate glucose reading, a more accurate assessment of the glycermic stage of a patient can be obtained and readily reported to the patient's physician.

As used herein, the term "glucose bias" is defined as a trend in the collection, analysis, interpretation, or review of glucose data from a glucose assay that leads to the conclusion that the patient's glucose level of the blood sample is systematically different from the patient's actual glucose level.

The inventive methods and devices generally reduce or eliminate the glucose bias caused by the different hematocrit levels of blood samples. Generally, when a blood sample has a low hematocrit level, the biosensor reagent gives an increasingly positive bias moving from low to high glucose levels. The bias effect is also dependent on the hematocrit level. In other words, the bias effect is noticeably more significant at a 20 Vol. % hematocrit level than at a 30 Vol. % hematocrit level. Conversely, when a blood sample has a high hematocrit level, the biosensor reagent generally gives increasingly negative bias moving from low to high glucose levels. In other words, the bias effect is more significant at a 60 Vol. % hematocrit level than at a 50 Vol. % hematocrit level. The methods and devices described herein accommodate the varying degrees of glucose bias which are obtained in blood samples depending on whether the sample has a low or high hematocrit level.

The present invention generally involves determining the glucose level of a blood sample, using the difference in resistivity or resistance between plasma and blood cells to determine the hematocrit level of the blood sample, and then using the calculated percent hematocrit level to adjust for the glucose bias, if one exists. The methods and devices described herein also provide a way of estimating the hematocrit value of blood samples using biosensor reagents.

More specifically, the present invention involves the acts of (1) measuring the glucose value, $Glu_m$, of the blood sample; (2) measuring the resistance of the blood sample ($R_{cell}$) using a biosensor reagent; (3) measuring the resistance of plasma ($R_{plasma}$) using a biosensor reagent; (4) determining the calculated resistance of red blood cells ($R_{RBC}$) by subtracting the resistance of plasma ($R_{plasma}$) from the resistance of the blood sample ($R_{cell}$); (5) calculating the percent hematocrit, % $Hct_c$, of the blood sample; (6) determining whether to adjust the glucose value, $Glu_m$, to an adjusted glucose value, $Glu_{adj}$; and (7) using the calculated percent hematocrit, % $Hct_c$, and either the glucose value, $Glu_m$, or the adjusted glucose value, $Glu_{adj}$, to adjust for the bias of the biosensor reagent, if any, which is caused by the glucose bias.

In another embodiment, the present invention involves the acts of (1) measuring the glucose value, $Glu_m$, of the blood sample; (2) measuring the cell resistance, $R_{cell}$, of the blood sample using a biosensor reagent; (3) measuring the plasma resistance, $R_{plasma}$, of the blood sample using a biosensor reagent; (4) determining the calculated resistance of red blood cells, $R_{RBC}$, of the blood sample according to the relationship:

$$R_{RBC}=R_{cell}-R_{plasma};$$

(5) calculating the percent hematocrit, % $Hct_c$, of the blood sample according to the relationship:

$$\%Hct_c=-k_1*(R_{RBC})^2+k_2*R_{RBC}+k_3$$

where $k_1$ ranges from about +100 to about −100, $k_2$ ranges from about +100 to about −100, and $k_3$ from about +100 to about −100; and (6) determining whether to adjust the glucose value, $Glu_m$; and (7) adjusting, if necessary, the glucose value, $Glu_m$, using the percent hematocrit, % $Hct_c$, and the glucose value $Glu_m$ according to the relationship:

$$Glu_{adj}=Glu_m+k_5$$

By using the present invention, the glucose level of a blood sample without the hematocrit bias or effect can be obtained and, hence, a more accurate assessment of a patient's glycermic stage may be obtained.

By using the methods and devices described herein, in situ hematocrit adjustments may be performed during glucose testing. By programming the equations described herein into software that is used with an electrochemical device or meter, in situ hematocrit adjustments may be performed. Alternatively, one or more pieces of data obtained from the equations described herein may be manually calculated and/or entered into the software that is used with the electrochemical device so that in situ hematocrit adjustments may be performed.

As the glucose level and hematocrit level can be measured at the same time using the inventive methods and devices, the hematocrit effect can be estimated and adjusted from the glucose value. The adjusted glucose value more accurately reflects the true glucose value and, hence, the true glycermic stage of the patient.

Typical biosensor reagents operate using electrochemical cells. For an electrochemical cell, the potential of the working electrode (WE) is the equilibrium value ($E°$) at open circuit (I=0). By applying an external voltage, a current is forced through the electrochemical cell and the potential of the working electrode shifts to a new value ($E''$). Assuming the reference electrode (RE) does not change its potential at the external current level, the potential difference between the equilibrium and new values ($E°$ and $E''$) is the potential drop, i.e., iR drop, in the test solution. This potential drop is characteristic of the bulk solution in the electrochemical cell.

As used herein, the term "biosensor reagent" includes any agent that can detect glucose in a blood specimen via an electrochemical reaction or a reaction by changing the optical property of the biosensor. Examples of suitable biosensor reagents for use in embodiments of this invention include, but are not limited to, DEX®, Espirit®, and Elite® biosensor reagents available from Bayer Corporation in Elkhart, Ind.; Precision® biosensor reagents available from MediSense in Abbott Park, Ill.; Accucheck® biosensor reagents available from Roche in Indianapolis, Ind.; and OneTouch® biosensor reagents available from Lifescan in Milpitas, Calif.

The inventive methods involve measuring the solution resistance or cell resistance ($R_{cell}$) of the blood sample between the reference electrode and the working electrode in a biosensor reagent such as a DEX® biosensor reagent. This is accomplished by applying a potential pulse, such as a 50 mV pulse. The current is measured at two time points after the pulse, and the initial current is calculated by exponential extrapolation to the time at which the pulse is applied. $R_{cell}$ is the blood resistance contributed by plasma and blood cells. Due to the differences in the physical properties of plasma and blood cells, plasma and blood cells exhibit differences in resistivity. When the blood cells increase (and the plasma decreases), the value of $R_{cell}$ increases. When the blood cells decrease (and the plasma increases), the value of $R_{cell}$ decreases.

The inventive methods further involve measuring the plasma resistance ($R_{plasma}$) between the reference electrode and the working electrode in a biosensor reagent. This is accomplished by applying a potential pulse such as 50 mV. This current is measured at two time points after the pulse, and the initial current is calculated by exponential extrapolation to the time at which the pulse is applied. $R_{cell}$ is calculated from the initial current and pulse amplitude using Ohm's law. $R_{plasma}$ depends on the components of the plasma (i.e., protein and electrolytes). $R_{plasma}$ does not vary with changing levels of hematocrit in a blood sample as there are no cells in plasma. Minor variations in the value of $R_{plasma}$ occur with different lots of reagents.

The value of $R_{plasma}$ can be electronically programmed into the software that is used with the electrochemical device or meter. The value of $R_{plasma}$ can also be included on a calibration chip provided with the biosensor reagent or included on a label located on the biosensor reagent. Alternatively, the value of $R_{plasma}$ can be predetermined for each lot of reagent during manufacturing and provided to the user or patient to be manually input by the user or patient into the electrochemical device or commercially available optical strip.

Electrochemical devices are instruments which read biosensor reagents. Examples of suitable electrochemical devices which may be used for reading biosensor reagents according to the present invention include, but are not limited to, the BAS 100B Analyzer available from BAS Instruments in West Lafayette, Ind.; the CH Instrument Analyzer available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J.

The inventive methods further involve determining the calculated resistance of the red blood cells, $R_{RBC}$, of a biosensor reagent according to the relationship set forth in Equation 2:

$$R_{RBC} = R_{cell} - R_{plasma} \quad \text{(Eq. 2)}$$

$R_{RBC}$ is the resistance difference between whole blood and plasma. A typical value of $R_{RBC}$ is approximately 1000 and may range from approximately 0 to approximately 500,000. Equation 2 can be electronically programmed into the software that is used with the electrochemical device or meter so that the value of $R_{RBC}$ may be calculated by the software. Alternatively, the value of $R_{RBC}$ may be calculated by the user or patient and may be manually input into the electrochemical device or commercially available optical strip.

The inventive methods further involve calculating the percent hematocrit, % $Hct_c$, of the blood sample according to the relationship set forth in Equation 3:

$$\% \, Hct_c = -k_1 * (R_{RBC})^2 + k_2 * R_{RBC} + k_3 \quad \text{(Eq. 3)}$$

It has been discovered that the hematocrit of whole blood has a polynomial relationship with the calculated percent hematocrit, % $Hct_c$. Specifically, the % $Hct_c$ is equal to a first constant, $k_1$, multiplied by the square of $R_{RBC}$ derived from Equation 2 plus a second constant, $k_2$, multiplied by $R_{RBC}$ plus a third constant, $k_3$.

First, second, and third constants, $k_1$, $k_2$, and $k_3$, may range from about +100 to about −100. In some embodiments, $k_1$ ranges from about +5 to about −5. In some embodiments, $k_2$ ranges from about +10 to about −10. In some embodiments, $k_3$ ranges from about +50 to about −50. First, second and third constants, $k_1$, $k_2$, and $k_3$, may be determined for each lot of biosensor reagent. The values for $k_1$, $k_2$, and $k_3$ can be determined using standard curve-fitting software. Specifically, the values of $R_{RBC}$ and % $Hct_c$, can be curve-fitted using a second order polynomial math conversation to determine the values for $k_1$, $k_2$, and $k_3$.

The values for $k_1$, $k_2$, and $k_3$ can be predetermined for each lot of reagent during manufacturing. The values for $k_1$, $k_2$, and $k_3$ can be electronically programmed into the software that is used with the electrochemical device. The values for $k_1$, $k_2$, and $k_3$ can also be provided to the user or patient who can manually input the values for $k_1$, $k_2$, and $k_3$ into the electrochemical device.

Equation 3 can be electronically programmed into the software that is used with the electrochemical device so that the value of % $Hct_c$ may be calculated by the software. Alternatively, the value of % $Hct_c$ may be calculated by the user or patient by using the values for $k_1$, $k_2$, and $k_3$ that are provided to the user or patient and manually input into the electrochemical device.

Ideally, the biosensor reagent exhibits no hematocrit effect and, consequently, no glucose bias. In an ideal situation where the biosensor reagent exhibits no hematocrit effect and no glucose bias, a plot of the percent of glucose bias versus the percent hematocrit calculated, % $Hct_c$, would produce a flat line with a slope equal to 0 and data points with are close to the line. Generally, however, due to RBC interference, a plot of the percent of glucose bias versus the percent hematocrit calculated, % $Hct_c$, for a typical biosensor reagent measurement produces a curve which is nonlinear.

The inventive methods further involve measuring the glucose level, $Glu_m$, of the whole blood sample. The measured glucose level, $Glu_m$, may be determined by art-recognized, conventional methods such as using glucose analyzers, for example a YSI 2300 Glucose and Lactate Analyzer or a STAT Plus Glucose & Lactate Analyzer available from YSI Incorporated in Yellow Springs, Ohio.

The inventive methods further involve determining whether to adjust the measured glucose value, Glum, and correcting the hematocrit bias of the measured glucose value to adjust for the hematocrit effect and, consequently, the glucose bias, if one exists. Using the value of % $Hct_c$, which is obtained from Equation 3 and the measured glucose level, $Glu_m$, which is determined by art-recognized, conventional methods, an adjustment or correction factor is determined.

Specifically, a correspondent adjustment may be made to $Glu_m$, if necessary, to adjust for the glucose bias of the biosensor reagent. The adjustment is performed using the relationship set forth in Equation 4:

$$Glu_{adj} = Glu_m + k_5 \quad \text{(Eq. 4)}$$

where Glum is obtained using art-recognized, conventional methods and $k_5$ is an adjustment factor. The values for $k_5$ may be included on a calibration chip provided with the biosensor reagent or included on a label located on the biosensor reagent. Alternatively, the values for $k_5$ may be provided to the user for programming into a home glucose monitor. The adjustment factor which is used to adjust for the glucose bias of the biosensor reagent may range from about −50% to about 50%. An adjustment is made to $Glu_m$ to adjust for the glucose bias of the biosensor reagent only if the calculated percent hematocrit, % $Hct_c$, level does not equal 40%. The normal hematocrit range for humans generally ranges from about 20% to about 60% and is centered around 40%. As a result, glucose sensors are calibrated at 40% whole blood and the slope and intercept at 40% hematocrit are used to calculate the glucose concentration. Thus, an adjustment is made to $Glu_m$ for the glucose bias of the biosensor reagent where the calculated percent hematocrit, % $Hct_c$, level does not equal 40%.

$Glu_{adj}$ represents the adjusted or corrected glucose value which is obtained upon performing the adjustment. The adjusted glucose value, $Glu_{adj}$, is a more accurate reflection of the patient's true glucose value and, hence, the patient's glycermic stage. Equation 4 can be electronically programmed into the software that is used with the electrochemical device.

By the methods and devices described herein, the measured glucose and hematocrit levels can be determined at the same time. Specifically, the computer can be programmed to calculate the values for $R_{cell}$ and $Glu_m$. The computer may be programmed to simultaneously calculate the values for $R_{cell}$ and $Glu_m$. From these values, the adjusted glucose value, $Glu_{adj}$, may be calculated.

By the methods and devices described herein, the calculated percent hematocrit, % $Hct_c$, and the glucose value, $Glu_m$, and/or the adjusted glucose value, $Glu_{adj}$, are used to adjust for the bias of the biosensor reagent, if any, which is caused by the glucose bias.

The methods and devices described herein also allow end users of glucometers to determine the true glucose value of blood samples conveniently and easily outside of the clinical or laboratory setting and without using clinical or laboratory equipment. The methods and devices described herein obviate the need to measure the percent hematocrit of the blood sample in a clinical or laboratory setting. The end users of the inventive methods and devices may be patients, physicians, or other health care professionals. Because the methods described herein allow a patient to determine the adjusted glucose value from home without waiting on test results from a laboratory or clinic, the patient can immediately relay his or her true glucose value to a physician.

It is contemplated that the methods described herein may be used with any system that uses electrochemical devices or cells for measuring the glucose level of a blood sample. For example, it is contemplated that the methods of the present invention may be used with home glucose-monitoring products, glucose-monitoring products used in a laboratory setting, or any other devices which employ electrochemical circuitry.

Also contemplated by the invention described herein are systems for use in practicing the subject invention. The subject systems are composed of biosensor reagents and meters. The meters typically include (a) means for measuring the glucose value, $Glu_m$, of the blood sample; (b) means for measuring the resistance of the blood sample ($R_{cell}$) using a biosensor reagent; (c) means for measuring the resistance of plasma ($R_{plasma}$) using a biosensor reagent; (d) means for determining the calculated resistance of red blood cells ($R_{RBC}$) by subtracting the resistance of plasma ($R_{plasma}$) from the resistance of the blood sample ($R_{cell}$); (e) means for calculating the percent hematocrit, % $Hct_c$, of the blood sample; (f) means for determining whether to adjust the glucose value, $Glu_m$, to an adjusted glucose value, $Glu_{adj}$; and (g) means for using the calculated percent hematocrit, % $Hct_c$, and the glucose value, $Glu_m$, or the adjusted glucose value, $Glu_{adj}$, to adjust for the bias of the biosensor reagent, if any, which is caused by the glucose bias.

The meters may also include (a) means for measuring the glucose value, $Glu_m$, of the blood sample; (b) means for measuring the cell resistance, $R_{cell}$, of the blood sample using a biosensor reagent; (c) means for measuring the plasma resistance, $R_{plasma}$, of the blood sample using a biosensor reagent; (d) means for determining the calculated resistance of red blood cells, $R_{RBC}$, of the blood sample according to the relationship:

$$R_{RBC} = R_{cell} - R_{plasma};$$

(e) means for calculating the percent hematocrit, % $Hct_c$, of the blood sample according to the relationship:

$$\%Hct_c = -k_1 * (R_{RBC})^2 + k_2 * R_{RBC} + k_3$$

where $k_1$ ranges from about +100 to about −100, $k_2$ ranges from about +100 to about −100, and $k_3$ from about +100 to about −100; (f) means for determining whether to adjust the glucose value, $Glu_m$; and (g) means for adjusting, if necessary, the glucose value, $Glu_m$, using the percent hematocrit, % $Hct_c$, and the glucose value $Glu_m$ according to the relationship:

$$Glu_{adj} = Glu_m + k_5$$

The following examples are given to exemplify embodiments of the invention. These examples should not be construed to limit the invention as otherwise described and claimed herein.

EXPERIMENTAL

Example 1

Hematocrit Effect on Glucose Measurement

This example illustrates the hematocrit effect (i.e., the bias reading derived from hematocrit content) that is observed in glucose biosensor reagents. To illustrate the variation in the measured glucose level that is obtained with whole blood samples having different hematocrit content, four aliquots of whole blood (Samples 1-4) were obtained and pooled together.

The hematocrit content of Samples 1-4 was adjusted to 20 Vol. %, 30 Vol. %, 50 Vol. %, and 60 Vol. % Hct, respectively, using the hematocrit adjustment protocol described below. The volume of plasma to be added to each of the four aliquots of whole blood (i.e., Samples 1-4) to achieve the target hematocrit contents (i.e., 20 Vol. %, 30 Vol. %, 50 Vol. %, and 60 Vol. % Hct) was calculated using the relationship set forth in Equation 5:

$$P = \left(\frac{Hct_o}{Hct_t}\right) - 1 \times V \quad \text{(Eq. 5)}$$

where

P=Volume of plasma to be added or subtracted from the volume of the whole blood sample (V)

V=Volume of the whole blood sample $Hct_o$=Observed hematocrit of the whole blood sample $Hct_t$=Target hematocrit of the whole blood sample To adjust the hematocrit content of Samples 1-4 to 20 Vol. %, 30 Vol. %, 50 Vol. %, and 60 Vol. % $Hct_t$, respectively, the values of P, V, $Hct_t$ listed in Table A below were used. The final volume for all levels was 15 mL.

TABLE A

Determination of Plasma Levels to be Added to Achieve Target Hematocrit Levels

| Sample No. | $Hct_o$ | $Hct_t$ | V (mL) | P (mL) |
|---|---|---|---|---|
| 1 | 40 | 20 | 7.5 | +7.5 |
| 2 | 40 | 30 | 10 | +5.0 |
| 3 | 40 | 50 | 18 | −3.0 |
| 4 | 40 | 60 | 20 | −5.0 |

Therefore, 7.5 mL of plasma had to be added to Sample 1 to achieve a target hematocrit level of 20 Vol. %; 5.0 mL of plasma had to be added to Sample 2 to achieve a target hematocrit level of 30 Vol. %; 3.0 mL of plasma had to be removed from Sample 3 to achieve a target hematocrit level of 50 Vol. %; and 5.0 mL of plasma had to be removed from Sample 4 to achieve a target hematocrit level of 60 Vol. %.

Glucose was also added to each of the four aliquots of whole blood (Samples 1-4) using the glucose addition or fortification protocol described below. For each of Samples 1-4, target whole blood glucose concentrations were set at 20 mg/dL, 50 mg/dL, 100 mg/dL, 200 mg/dL, and 600 mg/dL. Each of Samples 1-4 was divided into aliquots which were each adjusted to blood glucose concentrations of 20 mg/dL, 50 mg/dL, 100 mg/dL, 200 mg/dL, and 600 mg/dL.

To determine the appropriate volume of 25% glucose stock to add to obtain the desired blood glucose concentration, the following equation (Equation 6) was used:

$$D = A(Glu_t - Glu_i)/Glu_{stock} \quad \text{(Eq. 6)}$$

where

A=Volume of blood sample to be fortified or spiked with glucose (mL)

$Glu_t$=Target blood glucose concentration (mg/dL) to be achieved through addition of glucose stock solution $Glu_i$=Initial blood glucose concentration (mg/dL)

$Glu_{stock}$=Blood glucose concentration of stock solution (25 g/dL)

D=Volume of 25% glucose stock solution (µL) to add to sample to obtain target blood glucose concentration The values for A, $Glu_t$, $Glu_i$, $Glu_{stock}$, and D at each of the target whole blood glucose concentrations are set forth in Table B below.

TABLE B

Calculation of Percent Glucose Stock Solution to Add to Obtain Target Glucose Concentration

| A (mL) | $Glu_t$ (mg/dL) | $Glu_i$ (mg/dL) | $Glu_{stock}$ (g/dL) | D (µL) |
|---|---|---|---|---|
| 2.5 | 20 | 8 | 25 | 1.2 |
| 2.5 | 50 | 8 | 25 | 4.2 |
| 2.5 | 100 | 8 | 25 | 10.0 |
| 2.5 | 200 | 8 | 25 | 19.2 |
| 2.5 | 600 | 8 | 25 | 59.2 |

The appropriate volume of 25% glucose stock solution was pipetted into each of Samples 1-4 to obtain the target blood glucose concentrations. Therefore, 1.2 µL of 25% glucose stock solution had to be added to Sample A to achieve a target blood glucose concentration of 20 mg/dL; 4.2 µL of 25% glucose stock solution had to be added to Sample B to achieve a target blood glucose concentration of 50 mg/dL; 10.0 µL of 25% glucose stock solution had to be added to Sample C to achieve a target blood glucose concentration of 100 mg/dL; 19.2 µL of 25% glucose stock solution had to be added to Sample D to achieve a target blood glucose concentration of 200 mg/dL; and 59.2 µL of 25% glucose stock solution had to be added to Sample E to achieve a target blood glucose concentration of 600 mg/dL.

The glucose levels (in mg/dL) of Samples 1-4 at each of the target whole blood glucose concentrations (i.e., the target glucose levels ($Glu_t$) of 20 mg/dL, 50 mg/dL, 100 mg/dL, 200 mg/dL, and 600 mg/dL achieved through the glucose addition protocol described above) were measured using two lots of DEX® biosensor reagents, Lots A and B. The target whole blood glucose concentrations ($Glu_t$) obtained using the glucose addition protocol described above are set forth in Table C below. The measured glucose values ($Glu_m$) of Samples 1-4 obtained from DEX® biosensor reagents lots A and B at varying measured percent hematocrit levels (% $Hct_m$) are also set forth in Table C below. The value of % $Hct_m$ may be calculated by the software or by the user or patient and manually input into the electrochemical device.

The DEX® biosensor reagent lots were programmed using a standard curve adjusted to 40 Vol. % Hct because it is the expected percent hematocrit (Vol. % Hct) for human blood samples.

TABLE C $Glu_m$ (mg/dL) at Varying % $Hct_m$ Levels

| $Glu_t$ (mg/dL) | Sample 1: 20 Vol. % $Hct_m$ | Sample 2: 30 Vol. % $Hct_m$ | Sample 3: 50 Vol. % $Hct_m$ | Sample 4: 60 Vol. % $Hct_m$ |
|---|---|---|---|---|
| DEX ® BIOSENSOR REAGENT, LOT A RESULTS | | | | |
| 20 | 21.1 | 15.3 | 14.2 | 26.1 |
| 50 | 50.6 | 45.3 | 48.3 | 59.0 |
| 100 | 99.65 | 98.59 | 94.29 | 91.67 |
| 200 | 204.8 | 199.8 | 186.7 | 187.5 |
| 600 | 615.1 | 605.3 | 585.4 | 577.2 |

TABLE C-continued

Glu$_m$(mg/dL) at Varying % Hct$_m$ Levels

| Glu$_t$ (mg/dL) | Sample 1: 20 Vol. % Hct$_m$ | Sample 2: 30 Vol. % Hct$_m$ | Sample 3: 50 Vol. % Hct$_m$ | Sample 4: 60 Vol. % Hct$_m$ |
|---|---|---|---|---|
| DEX ® BIOSENSOR REAGENT, LOT B RESULTS | | | | |
| 20 | 19.8 | 14.0 | 14.6 | 30.5 |
| 50 | 47.8 | 48.3 | 47.7 | 45.4 |
| 100 | 102.1 | 99.1 | 95.6 | 96.8 |
| 200 | 206.8 | 201.1 | 186.4 | 190.7 |
| 600 | 613.6 | 605.0 | 584.5 | 575.9 |

Although the measured glucose levels, Glu$_m$, theoretically should be the same as the target added glucose levels, Glu$_t$, obtained using the glucose addition protocol, the measured glucose levels, Glu$_m$, varied as shown in Table C depending upon the measured hematocrit level, % Hct$_m$, of a given sample. The percent glucose bias readings (i.e., the difference between the measured glucose values levels, Glu$_m$, and the target added glucose levels, Glu$_t$) that were obtained at varying measured percent hematocrit (% Hct$_m$) levels from Lots A and B for Samples 1-4 are set forth in Table D below:

TABLE D

Calculated Percent Glucose Bias Obtained at Varying % Hct$_m$ Levels

| Glu$_t$ (mg/dL) | Sample 1: 20 Vol. % Hct$_m$ | Sample 2: 30 Vol. % Hct$_m$ | Sample 3: 50 Vol. % Hct$_m$ | Sample 4: 60 Vol. % Hct$_m$ |
|---|---|---|---|---|
| DEX ® BIOSENSOR REAGENT, LOT A RESULTS | | | | |
| 20 | 1.1 | −4.7 | −5.8 | 6.1 |
| 50 | 0.6 | −4.7 | −1.7 | 9.0 |
| 100 | −0.35 | −1.41 | −5.71 | −8.33 |
| 200 | 4.8 | −0.2 | −13.3 | −12.5 |
| 600 | 15.1 | 5.3 | −14.6 | −22.8 |
| DEX ® BIOSENSOR REAGENT, LOT B RESULTS | | | | |
| 20 | −0.2 | −6.0 | −5.4 | 10.5 |
| 50 | −2.2 | −1.7 | −2.3 | 4.6 |
| 100 | 2.1 | −0.9 | −4.4 | −3.2 |
| 200 | 6.8 | 1.1 | −13.6 | −9.3 |
| 600 | 13.6 | 5.0 | −15.5 | −24.1 |

As shown in Tables C and D, the samples containing lower hematocrit levels generally provided an increasingly positive bias as the level of added glucose increased. This effect, for example, was more significant at 20 Vol. % Hct than at 30 Vol. % Hct. Also as shown in Tables C and D, the samples containing higher hematocrit levels generally provided an increasingly negative glucose bias as the level of added glucose increased. This effect, for example, was more significant at 60 Vol. % Hct than at 50 Vol. % Hct.

The percent glucose bias was plotted versus the average measured percent hematocrit, % Hct$_m$, at the 600 mg/dL glucose concentration at the averaged hematocrit levels from Table D above. In other words, the values shown in Table E were plotted in FIG. 1:

TABLE E

Average Calculated Percent Glucose Bias Obtained at Varying % Hct$_m$ Levels from Lots A and B

| Glu$_t$ (mg/dL) | Sample 1: 20 Vol. % Hct$_m$ | Sample 2: 30 Vol. % Hct$_m$ | Sample 3: 50 Vol. % Hct$_m$ | Sample 4: 60 Vol. % Hct$_m$ |
|---|---|---|---|---|
| 600 | 14.35 | 5.15 | −15.05 | −23.45 |

Example 2

Derivation of Hematocrit Adjustment Factor for Glucose

This example explains the derivation process for one embodiment of Equation 3 described above. Six whole blood samples were obtained and were divided into Samples 5-10. Using the hematocrit adjustment protocol set forth in Example 1 above, the hematocrit contents of Samples 5-10 were adjusted to 20 Vol. %, 30 Vol. %, 40 Vol. %, 45 Vol. %, 50 Vol. %, and 60 Vol. % Hct respectively (i.e., the measured percent hematocrit, % Hct$_m$, levels). The measured percent hematocrit, % Hct$_m$, levels (i.e., the 20 Vol. %, 30 Vol. %, 40 Vol. %, 45 Vol. %, 50 Vol. %, and 60 Vol. % Hct$_m$ levels) were obtained by measurement on a Compur M1100 micro-centrifuge.

Using three lots of DEX® biosensor reagents (Lots C, D, and E) and a BAS 100B Analyzer electrochemical device, the resistance of the blood sample (R$_{cell}$) and the resistance of plasma (R$_{plasma}$) of Samples 5-10 were measured. The test potential of the working electrode was 400 mV, and the glucose concentration was about zero for each run. The values for R$_{cell}$ for Lots C-E at varying measured percent hematocrit (% Hct$_m$) levels are set forth in Table F below:

TABLE F

R$_{cell}$ of Whole Blood at Varying Measured Percent Hematocrit (% Hct$_m$) Levels

| DEX ® Biosensor Reagent Lot | Sample 5: 20 Vol. % Hct$_m$ | Sample 6: 30 Vol. % Hct$_m$ | Sample 7: 40 Vol. % Hct$_m$ | Sample 8: 45 Vol. % Hct$_m$ | Sample 9: 50 Vol. % Hct$_m$ | Sample 10: 60 Vol. % Hct$_m$ |
|---|---|---|---|---|---|---|
| C | 1046 | 989 | 1091 | 1055 | 1079 | 1286 |
| D | 983 | 1036 | 1076 | 1111 | 1111 | 1219 |
| E | 984 | 1013 | 1089 | 1077 | 1132 | 1297 |

The values for R$_{plasma}$ for four replicates of Lots C-E are set forth in Table G below. The values for R$_{plasma}$ did not vary with varying measured percent hematocrit (% Hct$_m$) levels as observed with the values for R$_{cell}$.

TABLE G

| DEX ® Biosensor Reagent Lot | R$_{plasma}$ of Whole Blood | | | |
|---|---|---|---|---|
| | Replicate 1 | Replicate 2 | Replicate 3 | Replicate 4 |
| C | 948 | 976 | 913 | 924 |
| D | 894 | 993 | 901 | 912 |
| E | 981 | 950 | 953 | 926 |

The average value for R$_{plasma}$ for each of the four replicates for each of Lots C-E was calculated at 939.

Using the values of $R_{cell}$ from Table F and the average $R_{plasma}$ value of 939 from the replicates in Table G, the values of $R_{RBC}$ for Samples 5-10 for Lots C-E were calculated using Equation 2:

$$R_{RBC} = R_{cell} - R_{plasma} \quad \text{(Eq. 2)}$$

The values for $R_{RBC}$ at varying measured percent hematocrit (% $Hct_m$) levels which were obtained from the calculations of Equation 2 are set forth in Table H below:

TABLE H

| | $R_{RBC}$ of Whole Blood at Varying Measured Percent Hematocrit (% $Hct_m$) Levels | | | | | |
|---|---|---|---|---|---|---|
| DEX® Biosens or Reagent Lot | Sample 5: 20 Vol. % $Hct_m$ | Sample 6: 30 Vol. % $Hct_m$ | Sample 7: 40 Vol. % $Hct_m$ | Sample 8: 45 Vol. % $Hct_m$ | Sample 9: 50 Vol. % $Hct_m$ | Sample 10: 60 Vol. % $Hct_m$ |
| C | 107 | 50 | 152 | 116 | 140 | 347 |
| D | 44 | 97 | 137 | 172 | 172 | 280 |
| E | 45 | 74 | 150 | 138 | 193 | 358 |

Using the values of $R_{RBC}$, the measured percent hematocrit (% $Hct_m$) levels (i.e., 20 Vol. %, 30 Vol. %, 40 Vol. %, 45 Vol. %, 50 Vol. %, and 60 Vol. % Hct respectively), and curve-fitting software, the values of $k_1$, $k_2$, and $k_3$ in Equation 3 were determined. Specifically, the values of $R_{RBC}$ and % $Hct_m$ were curve-fitted using a second order polynomial math conversion via Slide Write Pro software manufactured by Advances Graphics Software, Inc. The values of $R_{RBC}$ were plotted on the x axis while the values of % $Hct_m$ were plotted on the y axis. The values of $k_1$, $k_2$, and $k_3$ that were obtained through the curve-fitting software are set forth in Table I below:

TABLE I

| Constant in Equation 3 | Value Determined From Curve-Fitting Software |
|---|---|
| k1 | −0.000397 |
| k2 | 0.285 |
| k3 | 9.63 |

The calculated percent hematocrit, % $Hct_c$, levels for Samples 5-10 for Lots C-E were then calculated using Equation 7:

$$\% Hct_c = -0.000397 * (R_{RBC})^2 + 0.285 * R_{RBC} + 9.63 \quad \text{(Eq 7)}$$

The calculated percent hematocrit, % $Hct_c$, levels which were obtained at the varying measured percent hematocrit levels using Equation 7 are set forth in Table J below:

TABLE J

| | Calculated Percent Hematocrit (% $Hct_c$) Levels at Varying Measured Percent Hematocrit Levels (% $Hct_m$) | | | | | |
|---|---|---|---|---|---|---|
| DEX® Biosens or Reagent Lot | Sample 5: 20 Vol. % $Hct_m$ | Sample 6: 30 Vol. % $Hct_m$ | Sample 7: 40 Vol. % $Hct_m$ | Sample 8: 45 Vol. % $Hct_m$ | Sample 9: 50 Vol. % $Hct_m$ | Sample 10: 60 Vol. % $Hct_m$ |
| C | 35.58 | 22.83 | 43.74 | 37.30 | 41.71 | 60.72 |
| D | 21.34 | 33.49 | 41.18 | 46.87 | 46.87 | 58.29 |
| E | 21.59 | 28.49 | 43.41 | 41.36 | 49.81 | 60.78 |

Figure 2:
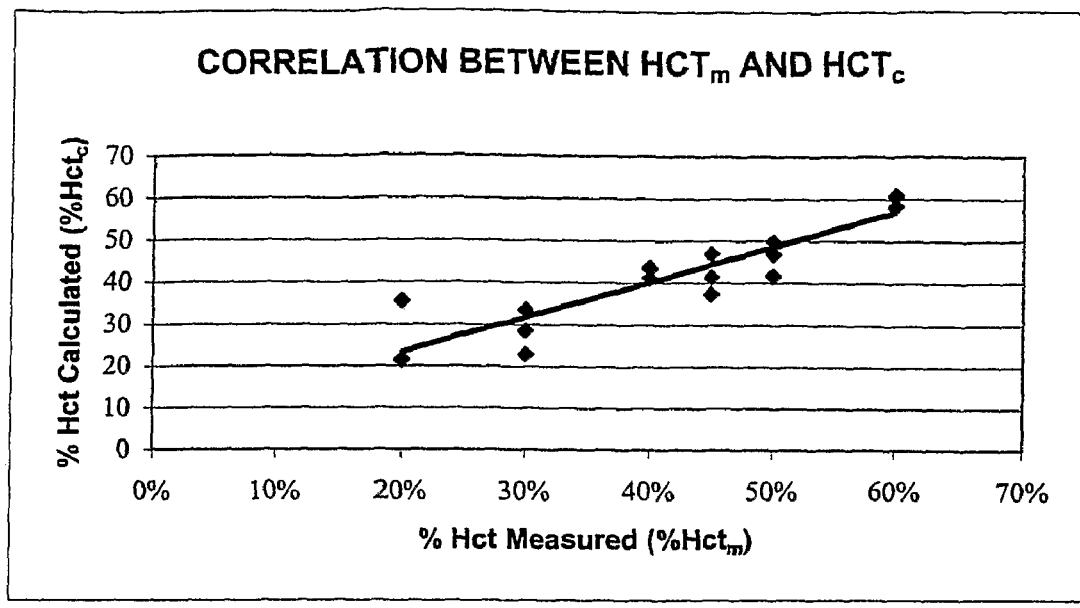
FIG. 2 is a plot of the percent hematocrit calculated (% $Hct_c$) versus the percent hematocrit measured (% $Hct_m$) for a series of whole blood samples.

A correlation curve between the measured percent hematocrit level (% $Hct_m$) and the calculated hematocrit level (% $Hct_c$) was prepared and is shown in FIG. 2. As shown in FIG. 2, the slope was 1.72 with an intercept of 26.3 while $R^2$ was 0.08311. $R^2$ is a correlation coefficient that reflects the degree of linearity of the plotted curve.

Example 3

Determination of Adjustment Factor

This example explains the process involved in determining the need for hematocrit correction, in determining the hematocrit correction factor, and in performing the hematocrit correction. The process begins by having a home glucose monitor user apply blood to an electrochemical sensor. The home glucose monitor will electrochemically determine the resistance of the blood sample, $R_{cell}$, using a biosensor reagent. The resistance of plasma, $R_{plasma}$, for the particular sensor lot will be electrochemically determined using a biosensor reagent by the manufacturer prior to shipment of the home glucose monitor. The value of $R_{plasma}$ will be stored in the calibration chip or label or will be provided to the user for programming into the home glucose monitor.

Using the values of $R_{cell}$ and $R_{plasma}$, the calculated resistance of red blood cells, $R_{RBC}$, is mathematically determined within the home glucose monitor. Once the $R_{RBC}$ has been determined, the percent hematocrit, % $Hct_c$, of the blood sample is determined within the home glucose monitor using Equation 3 set forth above. The values for $k_1$, $k_2$, and $k_3$ will be determined by the manufacturer using standard curve-fitting software. The values for $k_1$, $k_2$, and $k_3$ will be electronically programmed by the manufacturer into the software that is used with the home glucose monitor or will be provided to the user for programming or manually inputting into the home glucose monitor.

The measured glucose level, $Glu_m$, is determined by art-recognized, conventional methods such as using a glucose analyzer. Once the % $Hct_c$ is determined, the value of $k_5$ can be determined from the graph in FIG. 1. The values from FIG. 1 may be stored on a calibration chip provided with the biosensor reagent or stored on a label located on the biosensor reagent or may be provided for the user for programming into the home glucose monitor.

The calculated percent glucose bias is also predetermined and programmed into the calibration chip or label. An example of this percent glucose bias is graphed and shown in FIG. 1. The following is an example of the calculations:

| | | | | |
|---|---|---|---|---|
| $R_{cell}$ | 984 | 1040 | 1297 | |
| $R_{RBC}$ | 45 | 101 | 358 | ($R_{RBC} = R_{cell} - R_{plasma}$) |
| % $Hct_c$ | 20% | 40% | 60% | |
| $Glu_m$ | 134 | 120 | 96.6 | |
| $k_5$ | −14 | 0 | 23.4 | |
| $Glu_{adj}$ | 120 | 120 | 120 | ($Glu_{adj} = Glu_m + k_5$) |

The values for $R_{RBC}$ were obtained from Equation 2 while the values for $Glu_{adj}$ were obtained from Equation 4 discussed above. This will be determined within the laboratory by determining the percent glucose bias at various glucose levels and hematocrit levels. An example of this determination is shown in Table C (the actual glucose, $Glu_m$, values) and Table D (percent glucose bias from expected value). These percent glucose bias values are plotted as shown in FIG. 1. These values, which need to be added for higher hematocrits or subtracted for lower hematocrits generated from FIG. 1, will be electronically stored within the calibration chip or label for each reagent lot.

Once the calculated percent hematocrit, % $Hct_c$, levels have been determined and if the calculated percent hematocrit, % $Hct_c$, level does not equal 40%, the stored percent glucose bias value (from FIG. 1) is electronically retrieved and is used to display the correct glucose value on the display screen of the home glucose monitor. The process involved in determining the need for hematocrit correction, in determining the hematocrit correction factor, and in performing the hematocrit correction is invisible to the user of the home glucose meter.

While the invention has been described with a number of embodiments, the scope of the invention is not intended to be limited by the specific embodiments. Various modifications, changes, and variations may be apparent from the foregoing descriptions without departing from the spirit and scope of the invention as defined in the appended claims.

What is claimed is:

1. A method for adjusting glucose bias, if any, of a blood sample in a glucose-monitoring product comprising the acts of:
   (a) measuring the glucose value, $Glu_m$, of the blood sample;
   (b) measuring the resistance of the blood sample, $R_{cell}$, using a biosensor reagent;
   (c) identifying the resistance of plasma, $R_{plasma}$, for a reagent lot of the biosensor reagent during manufacturing;
   (d) determining the calculated resistance of red blood cells, $R_{RBC}$, of the blood sample according to the relationship:

$R_{RBC}=R_{cell}-R_{plasma}$;

(e) calculating the percent hematocrit, % $Hct_c$, of the blood sample using the calculated resistance of red blood cells $R_{RBC}$;
   (f) determining whether to adjust the glucose value, $Glu_m$, to an adjusted glucose value, $Glu_{adj}$ using the percent hematocrit, % $Hct_c$; and
   (g) using the percent hematocrit, % $Hct_c$, and the glucose value, $Glu_m$, or the adjusted glucose value, $Glu_{adj}$, from either act (a) or act (f) to adjust for the glucose bias of the blood sample, if any.

2. The method of claim 1, wherein the act of measuring the glucose value, $Glu_m$, of the blood sample involves using a laboratory glucose analyzer.

3. The method of claim 1, wherein the values of $R_{RBC}$ and % $Hct_c$ are manually calculated.

4. The method of claim 1, wherein the values of $R_{RBC}$ and % $Hct_c$ are determined by software used with the glucose-monitoring product.

5. The method of claim 1, wherein the act of measuring $R_{cell}$ involves measuring the cell resistance of the blood sample between a reference electrode and a working electrode in the biosensor reagent.

6. The method of claim 1, wherein the value of $R_{plasma}$ is electronically programmed into software used with the glucose-monitoring product.

7. The method of claim 1, wherein the value of $R_{plasma}$ is included on a calibration chip provided with the biosensor reagent.

8. The method of claim 1, wherein the value of $R_{plasma}$ is included on a label located on the biosensor reagent.

9. The method of claim 1, wherein the $R_{plasma}$ involves inputting a predetermined value by a user into the glucose-monitoring product.

10. The method of claim 1, wherein the value of $R_{RBC}$ is calculated by software used with the glucose-monitoring product.

11. The method of claim 1, wherein the value of $R_{RBC}$ is calculated manually and input into the glucose-monitoring product.

12. The method of claim 1, wherein the value of % $Hct_c$ is calculated by software used with the glucose-monitoring product.

13. The method of claim 1, wherein the value of % $Hct_c$ is calculated manually and input into the glucose-monitoring product.

14. The method of claim 1, wherein the blood sample is a whole blood sample.

15. A method for adjusting glucose bias, if any, of a blood sample in a glucose-monitoring product, the method comprising the acts of:
   measuring the glucose value, $Glu_m$, of the blood sample;
   measuring the cell resistance, $R_{cell}$, of the blood sample using a biosensor reagent;
   measuring the plasma resistance, $R_{plasma}$, of the biosensor reagent;
   determining the calculated resistance of red blood cells, $R_{RBC}$, of the blood sample according to the relationship:

$R_{RBC}=R_{cell}-R_{plasma}$;

calculating the percent hematocrit, % $Hct_c$, of the blood sample according to the relationship:

% $Hct_c = -k_1*(R_{RBC})^2 + k_2*R_{RBC} + k_3$ where $k_1$ ranges from about +100 to about −100, $k_2$ ranges from about +100 to about −100, and $k_3$ ranges from about +100 to about −100;
   determining whether to adjust the glucose value, $Glu_m$, using the percent hematocrit, % $Hct_c$; and
   adjusting, if necessary, the glucose value, $Glu_m$, using the percent hematocrit, % $Hct_c$, to obtain the adjusted glucose value $Glu_{adj}$ according to the relationship:

$Glu_{adj}=Glu_m+k_5$, wherein $k_5$ is an adjustment factor so as to adjust the glucose bias, if any, of the blood sample.

16. The method of claim 15, wherein the act of measuring the glucose value, $Glu_m$, of the blood sample involves using a laboratory glucose analyzer.

17. The method of claim 15, wherein the values of $R_{RBC}$ and % $Hct_c$ are manually calculated.

18. The method of claim 15, wherein the values of $R_{RBC}$ and % $Hct_c$ are determined by software used with the glucose-monitoring product.

19. The method of claim 15, wherein the act of measuring $R_{cell}$ involves measuring the cell resistance of the blood sample between a reference electrode and a working electrode in the biosensor reagent.

20. The method of claim 15, wherein the value of $R_{plasma}$ is electronically programmed into software used with the glucose-monitoring product.

21. The method of claim 15, wherein the value of $R_{plasma}$ is included on a calibration chip provided with the biosensor reagent.

22. The method of claim 15, wherein the value of $R_{plasma}$ is included on a label located on the biosensor reagent.

23. The method of claim 15, wherein the act of measuring $R_{plasma}$ involves inputting a predetermined value by a user into the glucose-monitoring product.

24. The method of claim 15, wherein the value of $R_{RBC}$ is calculated by software used with the glucose-monitoring product.

25. The method of claim 15, wherein the value of $R_{RBC}$ is calculated manually and input into the glucose-monitoring product.

26. The method of claim 15, wherein the value of % $Hct_c$ is calculated by software used with the glucose-monitoring product.

27. The method of claim 15, wherein the value of % $Hct_c$ is calculated manually and input into the glucose-monitoring product.

28. The method of claim 15, wherein the blood sample is a whole blood sample.

* * * * *